United States Patent [19]

Werner et al.

[11] Patent Number: 4,739,104

[45] Date of Patent: Apr. 19, 1988

[54] PROCESS FOR THE PREPARATION OF PIVALOYLPYRUVIC ACID ESTERS

[75] Inventors: Friedrich Werner, Cologne; Heinz Blank, Odenthal, both of Fed. Rep. of Germany

[73] Assignee: Bayer Aktiengesellschaft, Leverkusen, Fed. Rep. of Germany

[21] Appl. No.: 494,675

[22] Filed: May 13, 1983

Related U.S. Application Data

[63] Continuation of Ser. No. 403,990, Aug. 2, 1982, abandoned, which is a continuation of Ser. No. 200,846, Oct. 27, 1982, abandoned.

[30] Foreign Application Priority Data

Nov. 12, 1979 [DE] Fed. Rep. of Germany ....... 2945657

[51] Int. Cl.$^4$ ................... C07C 67/343; C07C 69/716
[52] U.S. Cl. ................... 560/174; 564/136
[58] Field of Search ......................... 560/174

[56] References Cited

PUBLICATIONS

Royals, J. Amer. Chem. Soc., vol. 67, 1508–1509 (1945).

Primary Examiner—Vivian Garner
Attorney, Agent, or Firm—Sprung Horn Kramer & Woods

[57] ABSTRACT

An improved process for the preparation of pivaloylpyruyic acid ester by reaction of pinacolin with an oxalic acid dialkyl ester followed by neutralization of the reaction mixture is disclosed, wherein the reactants are mixed at a temperature of −50° to +50° C. and the reaction completed at a temperature of 35° to 200° C.

6 Claims, No Drawings

PROCESS FOR THE PREPARATION OF PIVALOYLPYRUVIC ACID ESTERS

This application is a continuation of application Ser. No. 403,990, filed Aug. 2, 1982, now abandoned which is a continuation of Ser. No. 200,846, filed Oct. 27, 1982 (now abandoned).

The invention relates to a process for the preparation of pivaloylpyruvic acid esters by Claisen condensation of pinacolin with oxalic acid esters.

The reaction of equimolar amounts of pinacolin, oxalic acid diethyl ester and sodium methylate in methanol at room temperature over a reaction time of about 20 hours, in which sulphuric acid was added to the reaction mixture for working up and the pivaloylpyruvic acid ethyl ester was then extracted with benzene and isolated after evaporating off the benzene by distillation, is known from J. Am. Chem. Soc. 67, 1508 (1945). This process has the following disadvantages: the long reaction time permits only a low space/time yield; and the expensive extraction and the use of benzene, which is damaging to health, are an obstacle to an industrial procedure. It is found that the pivaloylpyruvic acid methyl ester which can be prepared by this process is obtained in a purity of only 83% and contains 15% of the ethyl ester. Such a product quality is unsatisfactory for a large number of possible uses. However, in the journal publication indicated, the use of sodium methylate is emphasized more than that of sodium ethylate, because the former is said to be easier to handle.

It is known, from Houben-Weyl, Methoden der organischen Chemie (Methods of Organic Chemistry), 4th edition, Volume VIII, page 566, 2nd paragraph (Georg Thieme Verlag Stuttgart, 1952), that if one of the reactants is a ketone, the ester condensation is carried out at as low as possible a temperature, the ketoneoxalo-ester always being prepared, in addition to other compounds, whilst cooling well.

A process has now been found for the preparation of pivaloylpyruvic acid esters by condensation of pinacolin with oxalic acid dialkyl esters in the presence of alcoholates as condensing agents, which is characterized in that the reactants mentioned are mixed at a temperature of $-50°$ to $+50°$ C., the reaction is brought to completion at a temperature of 35° to 200° C. and the reaction mixture be is treated with mineral acid in a manner which is in itself known.

Examples which may be mentioned of oxalic acid dialkyl esters for the process according to the invention are those of the formula

$$R^1O-CO-CO-OR^1 \qquad (I)$$

in which
    $R^1$ denotes alkyl or cycloalkyl.

Alkyl radicals which may be mentioned are straight-chain or branched aliphatic hydrocarbon radicals with 1 to 10 carbon atoms, such as methyl, ethyl, propyl, isopropyl, butyl, isobutyl, hexyl, octyl and decyl. Preferred alkyl is alkyl with 1 to 4 carbon atoms. Methyl and ethyl are particularly preferred.

Cycloalkyl radicals which may be mentioned are, for example, cycloaliphatic radicals which have 3 to 8 carbon atoms and are optionally substituted by methyl or ethyl, such as cyclopropyl, cyclobutyl, cyclopentyl, cyclohexyl, cycloheptyl and cyclooctyl. Preferred cycloalkyl radicals are cyclopentyl and cyclohexyl.

Of the oxalic acid diesters of the formula (I), oxalic acid dimethyl ester and oxalic acid diethyl ester are preferably employed in the process according to the invention, and oxalic acid dimethyl ester is particularly preferably employed.

Asymmetric oxalic acid dialkyl esters, that is to say those in which the oxalic acid is esterified with two different alcohols, can, of course, also be employed in the process according to the invention, but the symmetric oxalic acid dialkyl esters are in general used.

Examples of alcoholates as condensing agents for the process according to the invention are those of the formula

$$(R^2O)_nM \qquad (II)$$

in which
    $R^2$ denotes alkyl or cycloalkyl,
    M is an alkali metal or alkaline earth metal and
    n is 1 or 2, according to the valency of the alkali metal or alkaline earth metal.

Alkyl or cycloalkyl $R^2$ can assume the same scope of meaning with the same preferred ranges as in the case of $R^1$, it being possible for $R^1$ and $R^2$ to be identical or different.

Examples of alkali metals which may be mentioned are lithium, sodium, potassium, rubidium and cesium. Examples of alkaline earth metals which may be mentioned are beryllium, magnesium, calcium, strontium and barium.

The index n assumes the value 1 in the case of an alkali metal and the value 2 in the case of an alkaline earth metal.

Alkali metal alcoholates are preferably used in the process according to the invention, and sodium alcoholates are particularly preferably employed. Sodium methylate or sodium ethylate are very particularly preferably used.

The reactants pinacolin, oxalic acid dialkyl ester and alcoholate are in general employed in equivalent amounts. However, the alcoholate can also be employed in a slight excess, for example 0.1 to 15, preferably 5 to 10, equivalent percent, relative to the oxalic acid dialkyl ester employed. This slight excess can be favorable if the pinacolin or oxalic acid dialkyl ester employed has a slight water content, which is consumed by the excess alcoholate. However, it is likewise possible to employ an excess of one or both of the other reactants. This is of significance, for example, if excess pinacolin serves as the solvent for the process according to the invention.

In principle, the process according to the invention can be carried out in the absence or presence of a solvent. In the absence of a solvent, the reaction mixture frequently assumes a pasty to solid consistency in the course of the reaction. In such a case, the process according to the invention is advantageously carried out, for example, in a grinding autoclave. However, it is preferable to carry out the process according to the invention in the presence of a solvent because the technology is simplified.

Solvents which may be mentioned for the process according to the invention, in addition to the excess pinacolin already referred to, are those which are inert under the reaction conditions, for example aliphatic, araliphatic or aromatic hydrocarbons, such as hexane, heptane, octane, petroleum fractions, benzene, toluene or xylene, aliphatic alcohols, such as methanol, ethanol, propanol or butanol, ethers, such as diethyl ether, tetrahydrofuran or dioxane, and aromatic halogenated hydrocarbons, such as chlorobenzene or dichlorobenzene.

If an alcohol is employed as the solvent for the process according to the invention, the alcohol which has also been utilized for the preparation of the alcoholate is preferably used. For example, it is possible to introduce the amount of alkali metal or alkaline earth metal required for the condensation reaction into excess alcohol and then to add the pinacolin and the oxalic acid dialkyl ester to this alcoholate solution.

However, the aliphatic, araliphatic or aromatic hydrocarbons and the halogenated aromatic hydrocarbons which are immiscible with water are preferably employed as solvents for the process according to the invention. From this group, those solvents which have boiling points higher than that of the alcohol split off in the condensation reaction are particularly preferably employed.

The reactants alcoholate, oxalic acid dialkyl ester and pinacolin can in principle be brought together in any desired sequence in the solvent used in the preferred process variant. It is thus possible, for example, to initially introduce the alcoholate in the solvent used and then to add the oxalic acid dialkyl ester and thereafter the pinacolin. However, a mixture of the oxalic acid dialkyl ester and pinacolin can also be added to the alcoholate, initially introduced in the solvent. It is furthermore possible to initially introduce a mixture of the oxalic acid dialkyl ester and pinacolin in the desired solvent and then to add the alcoholate, if appropriate dissolved or suspended in a further portion of the solvent.

The reactants are mixed, for example, at a temperature of $-50°$ to $+50°$ C., preferably of $-30°$ to $+30°$ C. and particularly preferably of $-10°$ to $+20°$ C. After bringing together the reactants, the reaction is brought to completion at a temperature of 35° to 200° C., preferably 40° to 140° C. and particularly preferably 45° to 120° C. The condensation reaction is very particularly preferably brought to completion at the boiling point of the lowest-boiling component of the reaction mixture.

The times for mixing the reactants and for the completion of the reaction depend largely on the amounts of the reactants and the volume of the reaction vessels. Times for the mixing which may be mentioned are those of from 10 minutes to 24 hours, preferably of from 30 minutes to 20 hours. As an example when carrying out the inventive process in an one liter laboratory flask, times for the mixing are those of from 30 to 120 minutes, preferably of from 45 to 90 minutes. As an example when carrying out the inventive process in a commercial vessel of from 5 to 20 m$^3$ volume, times for the mixing are those of from 3 to 20 hours, preferably of from 4 to 15 hours, depending somewhat on the volume of the vessel and the cross-section of the feed pipes.

Times for the completion of the reaction which may be mentioned are those of from 10 minutes to 24 hours, preferably of from 15 minutes to 20 hours. As an example when carrying out the inventive process in an one liter laboratory flask, times for the completion are those of from 15 minutes to 8 hours, preferably of from 20 minutes to 6 hours. As an example when carrying out the inventive process in a commercial vessel of from 5 to 20 m$^3$ volume, times for the completion are those of from 4 to 20 hours, preferably of from 5 to 12 hours, depending somewhat on the volume of the vessel and including the time for raising the temperature from the mixing stage to the completion stage.

The process according to the invention can in principle be carried out under normal pressure, reduced pressure or increased pressure, preferably under normal pressure. In the case where the condensation reaction is to be brought to completion at the boiling point of the lowest-boiling component of the reaction mixture, this boiling point can be adjusted to the desired value by applying a reduced pressure, for example of between 0.1 and 1 bar, or an increased pressure, for example of between 1 to 5 bars.

The alkali metal salt or alkaline earth metal salt of the pivaloylpyruvic acid ester is first formed in the condensation reaction. The reaction mixture is then treated with mineral acid in a manner which is in itself known in order to form the free pivaloylpyruvic acid ester.

The condensation and subsequent acid treatment in the process according to the invention may be illustrated by the following equations, using the reaction of pinacolin, oxalic acid dimethyl ester and sodium methylate as an example:

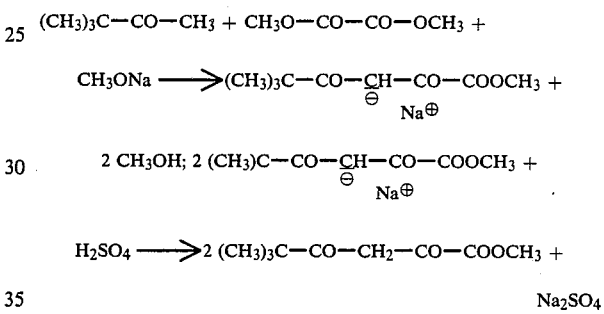

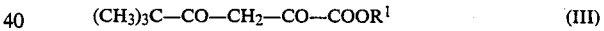

Accordingly, pivaloylpyruvic acid esters of the formula $$(CH_3)_3C-CO-CH_2-CO-COOR^1 \qquad (III)$$

in which

R$^1$ has the abovementioned meaning, can be prepared in the process according to the invention.

In principle, the reaction mixture which is obtained in the condensation reaction can be treated with mineral acid without other pre-treatment. Examples of mineral acids which may be mentioned are hydrochloric acid, nitric acid, phosphoric acid and sulphuric acid, preferably sulphuric acid. The mineral acid can be used as a concentrated or dilute acid. It is preferably used as a dilute acid, and particularly preferably as a dilute aqueous acid. The water content of the aqueous mineral acid can vary within wide limits, for example from 20 to 99% by weight, preferably 50 to 90% by weight, relative to the total amount of aqueous mineral acid. The amount of mineral acid is in general chosen such that the alkali metal salt or alkaline earth metal salt employed as the alcoholate is neutralized.

During the treatment with mineral acid, a multi-phase mixture which contains the free pivaloylpyruvic acid ester, the alkali metal salt or alkaline earth metal salt formed from the mineral acid, in dissolved or precipitated form, depending on the solubility of the salt and the water content of the mixture, the alcohol formed during the condensation or, if R$^1$ and R$^2$ are different, the alcohols formed, and, if appropriate, water and the solvent used during the condensation, is obtained. This mixture can be further treated, for example by filtering off precipitated salts or extracting the free pivaloylpyruvic acid ester, for example with benzene.

However, this procedure presents difficulties as a result of the salt precipitates in some cases being smeary and difficult to filter, and as a result of the expensive separation of the various phases formed during the extraction.

It has now been found that the difficulties in treating the reaction mixture formed in the condensation reaction with mineral acid can be eliminated by at least partly removing the alcoholic constituents from the reaction mixture before the treatment with mineral acid. Essentially complete removal of the alcoholic constituents is preferred.

This can be effected, for example, by simple distillation or by azeotropic distillation. If an alcohol is used as the solvent, for example, the solvent alcohol and the alcohol formed by the condensation can thus be distilled off from the reaction mixture when the reaction has ended. In cases where a non-alcoholic solvent is used, however, it is also possible already to distil off the alcohol formed in the condensation reaction or, if $R^1$ and $R^2$ are different, the alcohols formed in the condensation reaction, from the reaction mixture during the condensation. In this procedure, the alcohol is distilled off from the reaction mixture either by itself or as a azeotropic mixture with the solvent used, depending on the nature of the solvent used. In such a case, the temperature of the reaction mixture can rise from the boiling point of the alcohol split off to the boiling point of the solvent used if no further alcohol is present in the reaction mixture towards the end of the condensation reaction.

The reaction mixture which has been freed from the alcohol or alcohols is then treated with mineral acid. Before the treatment with mineral acid, the reaction mixture can also be present as a solution or suspension in a water-immiscible solvent. This latter variant is preferred. For this variant, after distilling off the alcoholic constituents, the distillation residue can be taken up in a water-immiscible solvent. Examples of water-immiscible solvents which can be used are the solvents mentioned above for the condensation reaction, with the exception of the alcoholic solvents given in that list. The hydrocarbons or aromatic halogenated hydrocarbons mentioned in the list are preferably used. Dissolving of the reaction mixture in the water-immiscible solvent is, of course, omitted if, in the preferred variant of the process according to the invention, such a solvent is already used for the condensation reaction and the alcoholic constituents are distilled out of this solution.

The water content of the aqueous mineral acid preferably employed should be sufficient to dissolve the salts, preferably the alkali metal salts and particularly preferably the sodium salts, formed during the neutralisation.

After the treatment with mineral acid, the aqeuous phase formed can be separated off from the organic phase formed. The pivaloylpyruvic acid ester contained in the organic phase can then be isolated by distillation.

Because of the increased reactivity of oxalic acid dimethyl ester compared with the esters of other alcohols, this ester has not hitherto been employed for the condensation with pinacolin even under the condensation conditions according to the state of the art. Condensation of pinacolin with oxalic acid dimethyl ester in th presence of sodium methylate to form pivaloylpyruvic acid methyl ester is thus a particular embodiment of the process according to the invention. This applies, in particular, to the variant in which solid oxalic acid dimethyl ester is added in molten form, from a heated stock vessel, to the reaction mixture at room temperature.

The process according to the invention is in general carried out by a procedure in which the alcoholate is initially introduced into the reaction vessel in the chosen solvent, the oxalic acid dialkyl ester is then added dropwise at a rate such that the batch is kept at the temperature required for mixing of the reactants, and finally the pinacolin is added to this mixture. The mixture is then heated to the chosen reaction temperature. The reaction has in some cases already ended within a few minutes, depending on the reactivity of the oxalic acid dialkyl ester with various alcohol radicals, which varies somewhat, the level of the reaction temperature and the chosen solvent. In the case where, in the preferred process variant, a water-immiscible solvent has already been chosen as the solvent for the condensation, the alcoholic constituents of the reaction mixture which are formed during the condensation reaction are already distilled out of the reaction mixture during the condensation, if appropriate together with a proportion of the water-immiscible solvent, by establishing an appropriately high reaction temperature.

When the condensation has ended, aqueous mineral acid is then added to the batch, which is dissolved in a water-immiscible solvent, in an amount which is sufficient to neutralise the metal ion of the alcoholate employed and to dissolve the resulting salt in the aqueous phase. For the treatment of the reaction mixture, dissolved in the water-immiscible solvent, with the aqueous mineral acid, the organic phase and the aqueous phase are vigorously mixed by intensively stirring. After the stirring, the aqueous phase and the organic phase separate completely. The aqueous phase is drained off and the organic phase is worked up by fractional distillation to isolate the pivaloylpyruvic acid ester.

According to the state of the art, it was to be expected that a decomposition reaction and a drastic reduction in yield would occur when the reaction temperature was increased. Surprisingly, it has been found that the condensation of pinacolin, oxalic acid dialky esters and an alcoholate can be carried out at elevated temperature, improved yield and shortened reaction times and thus a considerably more favourable space/time yield being achieved.

Moreover, the process according to the invention is carried out with the aid of simple measures which are also easy to implement in chemical technology; for example, during working up, the extraction required according to the state of the art is unnecessary in the process according to the invention.

The pivaloylpyruvic acid esters prepared by the process according to the invention are precursors for the preparation of pivaloylacetic acid esters. Thus, for example, a mixture of pivaloylpyruvic acid methyl ester with about 1/10 of its amount of powdered glass can be heated to about 175° C. and pyrolyzed in the course of about 5½ hours, carbon monoxide being split off, to give pivaloylacetic acid methyl ester (U.S. Pat. No. 2,527,306). The pivaloylacetic acid ester can then be further reacted with equimolar amounts of aniline or substituted anilines by heating in boiling xylene for about one hour to give optionally substituted α-pivaloylacetanilides, which are couplers for yellow dyestuffs in color photography (U.S. Pat. No. 3,265,506).

EXAMPLE 1

(for comparison)

23 g of sodium are dissolved in 300 ml of absolute methanol according to the instructions in J. Am. Chem. Soc. 67, 1508 (1945). A mixture of 1 mol of oxalic acid diethyl ester and 1 mol of pinacolin is then added dropwise to the sodium methylate solution, which is kept at room temperature by cooling, in the course of 1 hour and with exclusion of atmospheric moisture. The mixture is stirred for a further 6 hours at room temperature and then left to stand overnight at room temperature. An ice-cold solution of 30 g of concentrated sulphuric acid in 200 ml of water is then added to the ice-cooled reaction batch. The mixture is stirred for 10 minutes, poured into 1 liter of water and then extracted with three 100 ml portions of benzene. The combined benzene extracts are washed twice with 100 ml of water each time and then separated by distillation. 127 g of reactions product which, according to analysis by gas chromatography, contains 83% by weight of pivaloylpyruvic acid methyl ester and 15% by weight of pivaloylpyruvic acid ethyl ester are obtained. The contents of methyl ester and ethyl ester in the 127 g amount of reaction product correspond to 56.7% and 9.5% of the theoretical yield.

EXAMPLE 2

146 g (1 mol) of oxalic acid diethyl ester are added dropwise to 367.2 g of a 20% strength sodium ethylate solution in ethanol at 5° C. in the course of one hour, whilst stirring. 100 g of technical grade pinacolin are allowed to run in and the mixture is stirred for a further 15 minutes. It is then heated to 80° C. and heated under reflux for 3 hours. The solution is subsequently evaporated to dryness in a rotary evaporator. The residue is suspended in 200 ml of toluene and the suspension is stirred with 253 g of aqueous sulphuric acid (20.9% strength by weight) at 50° C. for 1 hour. The organic phase is separated off and distilled. 177 g of pivaloylpyruvic acid ethyl ester (88.2% of the theoretical yield) are obtained with a purity of 99.6% (by analysis by gas chromatography).

EXAMPLE 3

68 g (1 mol) of solid sodium ethylate are suspended in 300 g of toluene. 146 g (1 mol) of oxalic acid diethyl ester are added dropwise at 20° C. in the course of one hour, and 100 g (1 mol) of pinacolin are then allowed to run in. The mixture is subsequently stirred for 15 minutes and 201 g of ethanol/toluene mixture are then distilled off over a 50 cm high packed column in the course of 3 hours, the bottom temperature rising from 70° to 110° C. The bottom product is cooled to 40° C. and stirred with 234.5 g of aqueous sulphuric acid (20.9% strength by weight) for 1 hour. Distillation of the organic phase over a Vigreux column gives, at boiling point$_{0.5}$: 75° C., 176.5 g of pivaloylpyruvic acid ethyl ester (87.1% of theoretical yield) with a purity of 98.7% (by analysis by gas chromatography).

EXAMPLE 4

116.6 g (2.16 mols) of sodium methylate are suspended in 400 g of toluene. 292 g (2 mols) of oxalic acid diethyl ester are added dropwise at 5°-20° C. in the course of one hour. 200 g of technical grade pinacolin are then allowed to run in rapidly. The mixture is subsequently stirred for 15 minutes; 247 g of a methanol/ethanol/toluene mixture are then distilled off in the course of 4 hours. The bottom temperature rises to 110° C. towards the end of the distillation. The bottom product is cooled to 40° C. and stirred with 506 g of aqueous sulphuric acid (20.9% strength by weight) for 1 hour. Separation of the phases and subsequent distillation of the organic phase gives 359 g of distillate which consists of pivaloylpyruvic acid ethyl ester to the extent of 92.9% and of pivaloylpyruvic acid methyl ester to the extent of 6.4% (89.6% of the theoretical yield).

EXAMPLE 5

73.4 g (1.08 mols) of sodium ethylate are suspended in 950 g of n-hexane. 146 g (1 mol) of oxalic acid diethyl ester are added dropwise at 0°-5° C. in the course of one hour. 100 g of technical grade pinacolin are then allowed to run in rapidly. The mixture is heated to 60° C. and stirred for 1 hour. Gas chromatography analysis of a sample treated with sulphuric acid shows that the condensation has ended. 812 g of a mixture of ethanol and n-hexane are distilled off over a 50 cm high packed column at a boiling point of 62° C. in the course of 30 hours, in order to completely remove the ethanol. 253 g of 20.9% strength sulphuric acid are stirred into the solution at the bottom of the column at 40° C. After separation of the phases and distillation of the organic phase, 180.4 g of pivaloylpyruvic acid ethyl ester (89.6% of the theoretical yield) are obtained, at boiling point$_1$: 80° C., with a purity of 99.3% (by analysis by gas chromatography).

EXAMPLE 6

54 g (1 mol) of sodium are suspended in 300 g of n-hexane. 118 g (1 mol) of oxalic acid dimethyl ester, warmed to 60° C., are added dropwise at 0°-5° C. in the course of 1 hour. 100 g of pinacolin are then added rapidly at the same temperature. The mixture is stirred at room temperature for 15 minutes and 222 g of a n-hexane/methanol mixture are then distilled off, at boiling point$_{760}$: 50° C., over a 50 cm high packed column in the course of 6 hours. 234.5 g of aqueous sulphuric acid (20.9% strength by weight) are stirred into the bottom product. Separation of the phases and subsequent distillation of the organic phase give, at boiling point$_8$: 105° C., 159 g of pivaloylpyruvic acid methyl ester (85.0% of the theoretical yield) with a purity of 99.4% (by analysis by gas chromatography).

EXAMPLE 7

118 g of oxalic acid dimethyl ester, warmed to 60° C., are added dropwise to a suspension of 59.4 g (1.1 mols) of sodium methylate in 200 g of toluene, cooled to 5° C., in the course of 1 hour, whilst stirring. 100 g (1 mol) of technical grade pinacolin are allowed to run rapidly into the mixture. The mixture is subsequently stirred for 15 minutes and 90 g of a methanol/toluene mixture are then distilled off, at boiling point$_{760}$: 67° to 100° C., over a packed column in the course of 3 hours. The bottom product is cooled to 40° C. and 258 g of 20.9% strength by weight aqeuous sulphuric acid are added. Phase separation is effected after thorough stirring for 1 hour. Distillation of the organic phase at boiling point$_{0.4}$: 75° C. gives 163.5 g of pivaloylpyruvic acid methyl ester (87.0% of the theoretical yield) with a purity of 99.0% (by analysis by gas chromatography).

EXAMPLE 8

When a mixture, heated to 50° C., of pinacolin and oxalic acid dimethyl ester was added and the procedure was otherwise the same as in Example 6, a amount of 166.7 g of pivaloylpyruvic acid methyl ester (89% of the theoretical yield) were obtained. Purity: 99.3%.

EXAMPLE 9

292 g of oxalic acid dimethyl ester, warmed to 60° C., are added dropwise to 396 g of methanolic sodium methylate solution (30% strength by weight) at 5° C. in the course of 1 hour. 200 g of technical grade pinacolin are then added rapidly. The mixture is stirred at 20° C. for 15 minutes and then at the reflux temperature for 3 hours.

The solution is concentrated to dryness in a rotary evaporator, the residue is taken up in 400 g of toluene and the toluene mixture is stirred with 516 g of 20.9% strength by weight aqueous sulphuric acid at 50° C. Separation of the phases and distillation of the organic phase gives 293 g of pivaloylpyruvic acid methyl ester (78.6% of the theoretical yield). Purity: 99.8%.

EXAMPLE 10

198 g of methanolic sodium methyate solution (30% strength by weight) are added to 400 g of chlorobenzene. The methanol is distilled off at 65° C. in the course of 1 hour. The mixture is cooled to 10° C. and 118 g (1 mol) of molten oxalic acid dimethyl ester are introduced in the course of 1 hour. Thereafter, 100 g (1 mol) of pinacolin are allowed to run in and the mixture is subsequently stirred at room temperature for 15 minutes. It is heated, and the methanol formed in the reaction is distilled off in the course of 2 hours. Neutralisation with sulphuric acid, separation of the phases and distillation of the organic phase gives 165 g of pivaloylpyruvic acid methyl ester (87.8% of the theoretical yield). Purity: 99.0%.

EXAMPLE 11

The procedure followed is analogous to Example 9, 300 g of xylene are employed as the solvent. Yield: 162.0 g (84.7% of the theoretical yield). Purity: 97.2%.

EXAMPLE 12

57.2 g (1.06 mols) of sodium methylate are suspended in 400 g of dehydrated pinacolin. 118 g of molten oxalic acid dimethyl ester are added dropwise to the suspension in the course of 1 hour. The temperature is kept at 10° C. during this addition. The mixture is subsequently stirred for 15 minutes and 84 g of a methanol/pinacolin mixture are then distilled off at 64° C. The bottom product is cooled to 50° C. and 252 g of aqueous sulphuric acid (20.9% strength by weight) are added. Separation of the phases and subsequent distillation of the organic phase gives 164.6 g of pivaloylpyruvic acid methyl ester (87.8% of the theoretical yield), purity: 99.3%.

What is clamed is:

1. In a process for the preparation of pivaloylpyruvic acid ester by condensation of pinacolin with an oxalic acid dialkyl ester in the presence of an alcoholate as condensing agent wherein the reaction mixture, following completion of the reaction, is treated with a mineral acid to effect neutralization, the improvement which comprises carrying out the process in the presence of a water immiscible organic solvent, removing alcoholic constituents from the reaction mixture during the process before the treatment with mineral acid, mixing the reactants at a temperature of −50° to +50° C. and completing the reaction at a temperature of +35° to 200° C.

2. A process according to claim 1 wherein the reaction components are mixed at a temperature of −30° to +30° C. and the reaction is brought to completion at a temperature of 40° to 140° C.

3. A process according to claim 1 wherein an aliphatic, araliphatic or aromatic hyrocarbon or a halogenated aromatic hydrocarbon, with a boiling point above that of the alcohol split off in the condensation reaction, is employed as solvent.

4. A process according to claim 1 wherein the pinacolin is subjected to condensation with oxalic acid dimethyl ester in the presence of sodium methylate.

5. A process according to claim 1 wherein said oxalic acid dialkyl ester has the formula

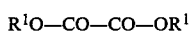

$$R^1O-CO-CO-OR^1$$

wherein $R^1$ denotes alkyl or cycloalkyl.

6. A process according to claim 5 wherein the alcholate has the formula

$$(R^2O)_nM$$

wherein $R^2$ denotes alkyl or cycloalkyl,

M is an alkali metal or alkaline earth metal and n is 1 or 2 according to the valency of the alkali metal or alkaline earth metal.

* * * * *